US008799767B2

(12) United States Patent
Craw et al.

(10) Patent No.: US 8,799,767 B2
(45) Date of Patent: Aug. 5, 2014

(54) TRANSFORMATION OF MEDICAL STATUS DATA INTO EXECUTABLE PROGRAMS

(75) Inventors: Chad E. Craw, Brooklyn, NY (US); Christopher M. Keegan, Marcellus, NY (US); James J. DelloStritto, Jordan, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 880 days.

(21) Appl. No.: 12/790,198

(22) Filed: May 28, 2010

(65) Prior Publication Data

US 2011/0295082 A1     Dec. 1, 2011

(51) Int. Cl.
*G06F 17/00*     (2006.01)
*G06F 17/22*     (2006.01)
*A61B 5/0205*    (2006.01)
*A61B 5/00*      (2006.01)
*H04L 29/08*     (2006.01)

(52) U.S. Cl.
CPC .......... *G06F 17/2247* (2013.01); *A61B 5/0205* (2013.01); *A61B 5/0002* (2013.01); *H04L 67/02* (2013.01)
USPC .......... 715/234; 600/301; 709/225; 709/229; 709/230

(58) Field of Classification Search
CPC . G06F 17/227; G06F 17/272; G06F 17/2247; G06F 17/2264; G06F 19/321; G06F 19/327; G06F 19/3406; G06F 19/3418; H04L 29/06; H04L 69/16; H04L 69/163; H04L 69/329; H04L 67/02
USPC .................. 715/234–236, 700, 760; 600/301; 709/225, 229, 230; 717/106, 115, 136, 717/140
See application file for complete search history.

(56) References Cited

U.S. PATENT DOCUMENTS

| | | | |
|---|---|---|---|
| 5,857,195 A | 1/1999 | Hayashi et al. | 707/999.102 |
| 6,505,086 B1 * | 1/2003 | Dodd et al. | 700/65 |
| 6,999,972 B2 | 2/2006 | Lusen et al. | 707/756 |
| 7,028,182 B1 | 4/2006 | Killcommons | 713/161 |
| 7,039,878 B2 | 5/2006 | Auer et al. | 715/810 |
| 7,043,752 B2 | 5/2006 | Royer et al. | 726/8 |
| 7,096,212 B2 | 8/2006 | Tribble et al. | 707/999.001 |
| 7,103,666 B2 | 9/2006 | Royer et al. | 709/227 |
| 7,188,121 B2 | 3/2007 | Tracey et al. | 707/999.102 |
| 7,233,987 B2 | 6/2007 | Watkinson | 709/223 |
| 7,234,002 B2 | 6/2007 | Lewis | 709/246 |

(Continued)

OTHER PUBLICATIONS

W. Richard Stevens, "TCP/IP Illustrated, vol. 1 the Protocols," © 1994 Addison Wesley Longman, Inc. Chapters 17-21, pp. 189-276.*

(Continued)

*Primary Examiner* — Chau Nguyen
*Assistant Examiner* — James H Blackwell
(74) *Attorney, Agent, or Firm* — Merchant & Gould P.C.

(57) ABSTRACT

A transformer system receives medical status data generated by a monitoring device. The medical status data represents one or more physiological characteristics of a patient. In response to receiving the medical status data, the transformer system applies a transformation to the medical status data. A script file results from the transformation of the medical status data. The transformation is specified by an Extensible Stylesheet Language Transformation (XSLT) document. The transformer system then executes the script file. When the transformer system executes the script file, the transformer system can perform various actions. For example, the transformer system can generate result data and provide the result data to one or more other systems.

17 Claims, 5 Drawing Sheets

(56) References Cited

U.S. PATENT DOCUMENTS

| | | | |
|---|---|---|---|
| 7,284,196 B2 | 10/2007 | Skeen et al. | 715/234 |
| 7,300,418 B2 | 11/2007 | Zaleski | 604/131 |
| 7,640,496 B1 * | 12/2009 | Chaulk et al. | 715/243 |
| 2003/0182305 A1 * | 9/2003 | Balva et al. | 707/103 R |
| 2004/0088374 A1 * | 5/2004 | Webb et al. | 709/218 |
| 2004/0243935 A1 * | 12/2004 | Abramovitch | 715/523 |
| 2006/0074465 A1 * | 4/2006 | Webb | 607/60 |
| 2006/0179421 A1 * | 8/2006 | Bielski et al. | 717/115 |

OTHER PUBLICATIONS

E.D. Zwicky et al.,"Building Internet Firewalls, $2^{nd}$ Edition," © 2000 O'Reilly Media, Inc. Chapters 1-4, pp. 3-101.*

* cited by examiner

TRANSFORMATION OF MEDICAL STATUS DATA INTO EXECUTABLE PROGRAMS

BACKGROUND

Monitoring devices are used frequently in today's hospitals to record or monitor various physiological characteristics of patients. Such patient monitoring devices generate medical status data. The medical status data represents a physiological parameter of a patient. For example, the medical status data can represent the blood pressure of a patient, a blood oxygen saturation level of the patient, a pulse rate of the patient, a body temperature of the patient, an electrocardiogram (ECG) of the patient, or other physiological parameters of the patient. Many patient monitoring devices have display screens to display such medical status data.

Furthermore, some monitoring devices have communication interfaces to communicate medical status data with other computing devices. For example, some patient monitoring devices have Universal Serial Bus (USB) interfaces, serial interface cards, Bluetooth network interfaces, WiFi interfaces, Ethernet interfaces, or other types of communication interfaces. In some instances, the patient status data generated by patient monitoring devices is not in a desired form. For example, the patient status data might not be in a format that is suitable for use by an Electronic Medical Records (EMR) system.

SUMMARY

A transformer system receives medical status data generated by a monitoring device. The medical status data represents one or more physiological characteristics of a patient. In response to receiving the medical status data, the transformer system applies a transformation to the medical status data. A script file results from the transformation of the medical status data. The transformation is specified by an Extensible Stylesheet Language Transformation (XSLT) document. A computing device then executes the script file. The computing device can perform various actions when the script file is executed. For example, execution of the script file can cause the computing device to transform the format of the medical status data. In another example, execution of the script file can cause the computing device to perform an analysis of the physiological characteristics of the patient based on the medical status data. Furthermore, in some instances, execution of the script file can cause the computing device to generate result data and provide that result data to one or more receiving systems.

DETAILED DESCRIPTION

Figure 1:
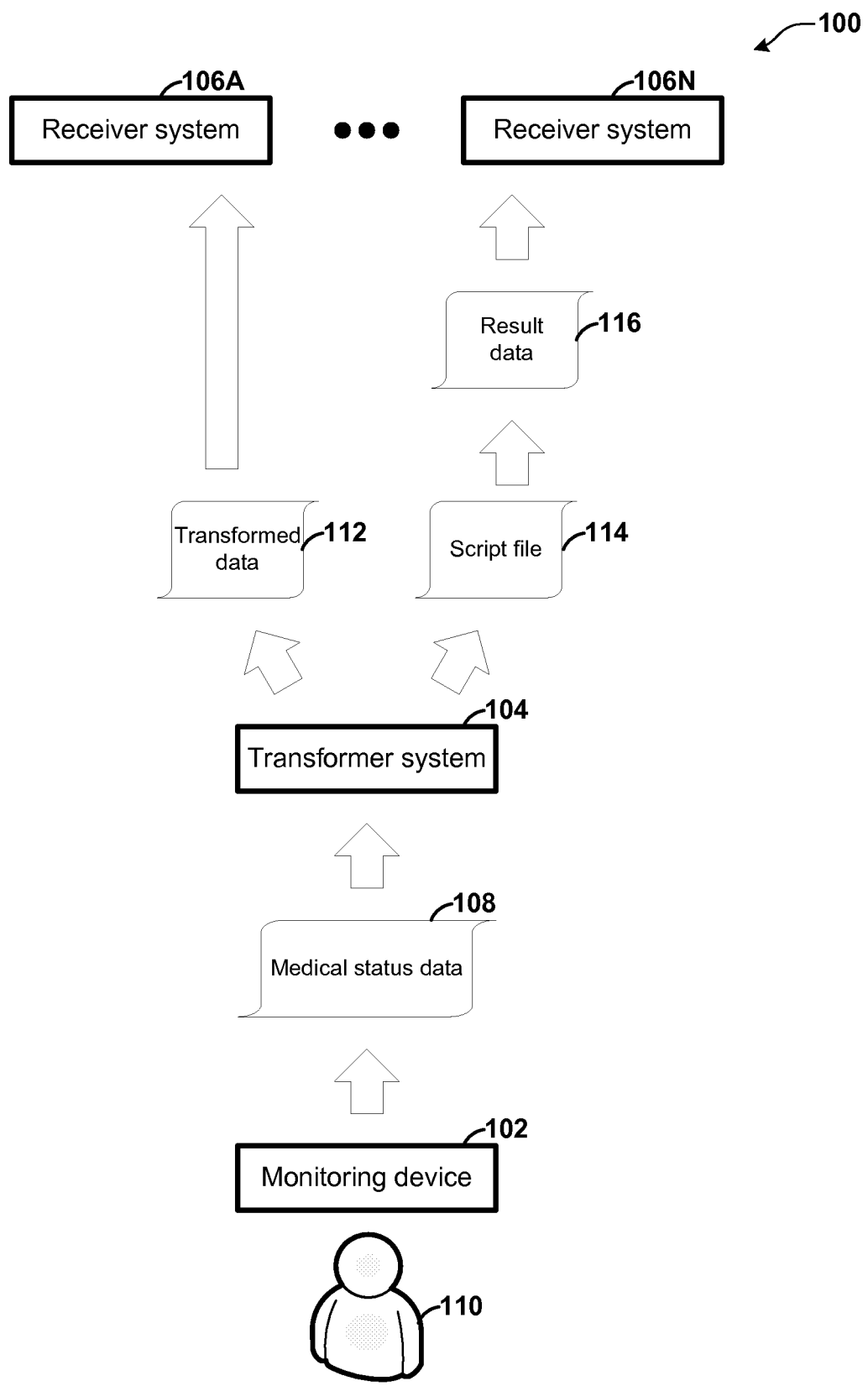
FIG. 1 is a block diagram illustrating an example system for generating and processing medical status data.

FIG. 1 is a block diagram illustrating an example system 100 for generating and processing medical status data. As illustrated in the example of FIG. 1, the system 100 includes a monitoring device 102, a transformer system 104, and a set of receiver systems 106A through 106N (collectively, "receiver systems 106"). It should be appreciated that in other embodiments, the system 100 can include additional devices and/or systems. For example, in some embodiments, the system 100 includes multiple monitoring devices and/or a single receiver system.

The monitoring device 102 is a device that generates medical status data 108. For example, the monitoring device 102 can be a Spot VITAL SIGNS® LXi vital signs device or a CP200™ electrocardiograph device manufactured by Welch Allyn, Inc. of Skaneateles, N.Y. The medical status data 108 represents one or more physiological characteristics of a patient 110. In various embodiments, the medical status data 108 can represent various physiological characteristics of the patient 110. For example, in some embodiments, the medical status data 108 can represent a blood pressure of the patient 110, a pulse rate of the patient 110, a body temperature of the patient 110, a blood oxygen saturation level of the patient 110, an electrocardiogram (ECG) of the patient 110, an electroencephalograph (EEG) of the patient 110, or other physiological characteristics of the patient 110.

The monitoring device 102 can use data from various instruments to generate the medical status data 108. For example, the monitoring device 102 can use data from blood pressure cuffs, finger clips, thermometers, electrodes, or other instruments to generate the medical status data 108. Such instruments can provide data to the monitoring device 102 in various ways. For example, such instruments can be included in the monitoring device 102, can be attached to the monitoring device 102, can be in wireless communication with the monitoring device 102, or can otherwise be able to provide data to the monitoring device 102.

Furthermore, in some embodiments, the monitoring device 102 displays information representing one or more physiological characteristics of the patient 110 on a display screen. For example, the monitoring device 102 can display numbers representing the current pulse rate of the patient 110 on a display screen. In this way, a person, such as a doctor or nurse, who is nearby the patient 110 can assess and monitor one or more physiological characteristics of the patient 110. The display screen can be incorporated into the monitoring device 102 or otherwise be in communication with the monitoring device 102.

In some circumstances, it is desirable to be able to store the medical status data 108 generated by the monitoring device 102, view the medical status data 108 generated by the monitoring device 102 remotely, or otherwise process the medical status data 108 generated by the monitoring device 102 remotely. Accordingly, the monitoring device 102 transmits the medical status data 108 to the transformer system 104. The transformer system 104 is a software system provided by one or more computing devices.

The transformer system 104 applies one or more transformations to the medical status data 108. The transformer system 104 can generate various types of data by applying various transformations to the medical status data 108. For example, the transformer system 104 can generate transformed data 112 by applying a transformation to the medical status data 108. The transformed data 112 is a transformed version of the medical status data 108. In this example, the transformed data 112 can have a different format than original version of the medical status data 108. In this example, the transformer system 104 can then provide the transformed data 112 to one or more of the receiver systems 106.

The receiver systems 106 are software systems provided by one or more computing devices. In some embodiments, the receiver systems 106 are provided by computing devices other than the computing device that provides the transformer system 104. In other embodiments, one or more of the receiver systems 106 are provided by the computing device that provides the transformer system 104. In various embodiments, the receiver systems 106 can perform various roles. For example, one or more of the receiver systems 106 can be electronic medical record (EMR) systems, hospital information systems (HIS), database systems, or other types of computing systems that provide for the storage and retrieval of data.

Furthermore, the transformer system 104 can generate a script file 114 by applying a transformation to the medical status data 108. In this example, one or more computing devices then execute the script file 114. When a computing device executes the script file 114, the script file 114 can cause the computing device to perform various actions. For example, the script file 114 can cause the computing device to present the medical status data 108 on a graphical user interface. In another example, the medical status data 108 represents a series of blood pressure readings. In this example, the script file 114 can cause the computing device to calculate a regression on the series of blood pressure readings. In yet another example, the script file 114 can cause the computing device to generate result data 116 and provide the result data 116 to one or more of the receiver systems 106.

In embodiments where the script file 114 causes the computing device to provide result data 116 to the receiver systems 106, the script file 114 can cause the computing device to transmit the result data 116 to one or more of the receiver systems 106 using various communication protocols. For example, the script file 114 can cause the computing device to transmit the result data 116 to one or more of the receiver systems 106 using a communication protocol that builds on the Transmission Control Protocol (TCP). Example communication protocols that build on TCP include the Hypertext Transfer Protocol (HTTP), the File Transfer Protocol (FTP), the SOAP protocol, and so on.

Figure 2:
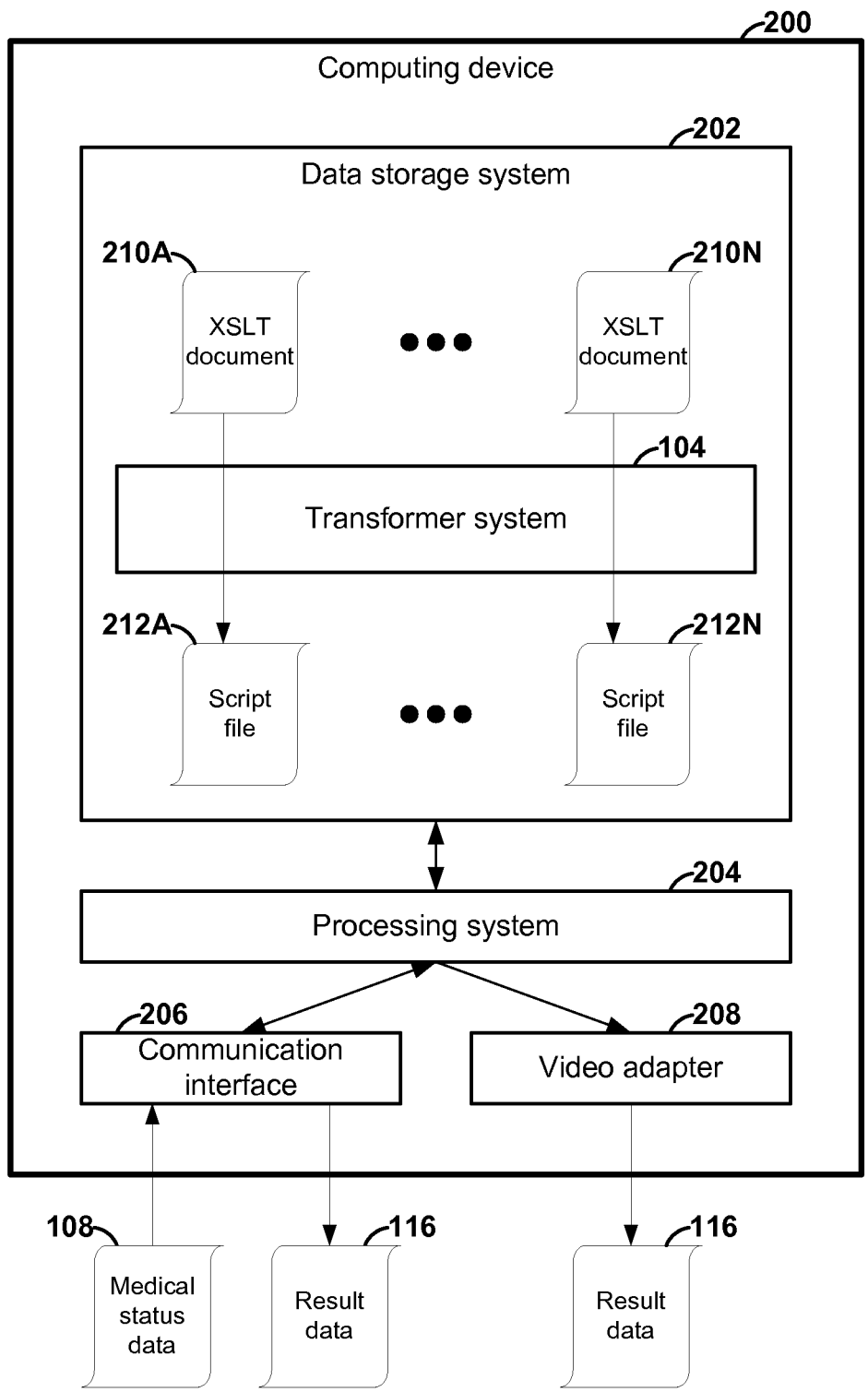
FIG. 2 is a block diagram illustrating example details of a computing device that provides a transformer system.

FIG. 2 is a block diagram illustrating example details of a computing device 200 that provides the transformer system 104. In various embodiments, the computing device 200 can be various types of computing devices. For example, in various embodiments, the computing device 200 can be a personal computer, a standalone server device, a blade server device, or another type of computing device.

As illustrated in the example of FIG. 2, the computing device 200 comprises a data storage system 202, a processing system 204, a communication interface 206, and a video adapter 208. The data storage system 202 is a system comprising one or more computer-readable storage media that are capable of storing data and computer-readable instructions. The processing system 204 is a system comprising one or more processing units that are capable of executing computer-readable instructions.

The communication interface 206 is a device that is capable of sending data to and receiving data from one or more other computing devices. In various embodiments, the communication interface 206 can be various types of devices that are capable of sending data to and receiving data from one or more other computing devices. For example, the communication interface 206 can be a network interface card, such as an Ethernet card. In another example, the communication interface 206 can be a Universal Serial Bus (USB) interface, a FireWire interface, a serial interface, a parallel port interface, or another type of device that uses a cable to send data to and receive data from one or more other computing devices. In yet another example, the communication interface 206 can be a wireless communication interface, such as a WiFi or Bluetooth interface.

As illustrated in the example of FIG. 2, the communication interface 206 can communicate with another device, such as the monitoring device 102, to receive the medical status data 108. The communication interface 206 can use various communication protocols when communicating with the other device to receive the medical status data 108. For example, the communication interface 206 can use the Welch Allyn Communication Protocol (WACP) when communicating with the monitoring device 102 to receive the medical status data 108. In another example, the communication interface 206 can use the SOAP protocol, the USB protocol, a serial protocol, or another protocol when communicating with the monitoring device 102 to receive the medical status data 108.

The data storage system 202 stores computer-readable instructions that, when executed by the processing system 204, cause the transformer system 104 to provide the transformer system 104. Furthermore, the data storage system 202 stores a set of Extensible Stylesheet Language Transformation (XSLT) documents 210A through 210N (collectively, "XSLT documents 210").

In some embodiments, the medical status data 108 is formatted according to the Extensible Markup Language (XML). XML is a markup language that allows developers to define their own tags. When the communication interface 206 receives the medical status data 108 formatted in XML, the transformer system 104 applies transformations specified by one or more of the XSLT documents 210 to the medical status data 108.

The transformer system 104 can generate various types of data by applying the transformations specified by the XSLT documents 210 to the medical status data 108. For example, the transformer system 104 can generate one or more versions of the medical status data 108 in various formats by applying transformations specified by one or more of the XSLT documents 210. In another example, the transformer system 104 can generate the script files 212A through 212N (collectively, "script files 212") by applying the transformations specified by the XSLT documents 210 to the medical status data 108. Application of transformations specified by different ones of the XSLT documents 210 to the same medical status data can result in the generation of different script files.

The following is an example transformation that could be specified by one of the XSLT documents 210:

```
<?xml version="1.0" encoding="UTF-8" ?>
- <xsl:stylesheet xmlns:xsl="http://www.w3.org/1999/XSL/Transform"
version="1.0"
xmlns:external="http://ExternalFunctions.DataCatcher.WelchAllyn.com"
exclude-result-prefixes="external">
    <xsl:output method="text" version="1.0" encoding="UTF-8"
indent="no" omit-xml-declaration="yes" />
    <xsl:variable name="pad" select="' '" />
    <xsl:variable name="pad-len" select="string-length($pad)" />
```

```
    <xsl:template match="/">
        <xsl:if test="function-available('external:output-filename')">
            <xsl:value-of select="external:output-filename('VBScript-', 'vbs', true( ))" />
        </xsl:if>
        <!-- Message Header -->
        <xsl:text>MsgBox("Data Object Received:" & vbCr & vbCr &</xsl:text>
        <!-- Date/Time of Message -->
        <xsl:text>"Current localtime:</xsl:text>
        <xsl:choose>
            <xsl:when test="function-available('external:localtime')">
                <when>
                    <xsl:value-of select="external:localtime( )" />
                </when>
            </xsl:when>
            <xsl:otherwise>
                <result>NO_LOCAL_TIME</result>
            </xsl:otherwise>
        </xsl:choose>
        <xsl:text>" & vbCr &</xsl:text>
        <!-- GUID -->
        <xsl:text>"Device GUID:</xsl:text>
    <xsl:choose>
        <xsl:when test="function-available('external:device-guid')">
            <when>
                <xsl:value-of select="external:device-guid( )" />
            </when>
        </xsl:when>
        <xsl:otherwise>
            <result>NO_GUID</result>
        </xsl:otherwise>
    </xsl:choose>
    <xsl:text>" & vbCr &</xsl:text>
    <!-- Patient Ientifier -->
    <xsl:text>"Patient ID:</xsl:text>
    <xsl:for-each select="DEFINITION/MEMBERS/MEMBER">
        <xsl:if test="contains(@class, 'Patient')">
            <xsl:for-each select="VALUE/DEFINITION/MEMBERS/MEMBER">
                <xsl:if test="@name = 'Identifier'">
                    <xsl:value-of select="VALUE" />
                </xsl:if>
            </xsl:for-each>
        </xsl:if>
    </xsl:for-each>
    <xsl:text>" & vbCr &</xsl:text>
    <!-- Clinician Ientifier -->
    <xsl:text>"Clinician ID:</xsl:text>
    <xsl:for-each select="/node( )/node( )/node( )/node( )/DEFINITION">
        <xsl:if test="contains(@class, 'Clinician')">
            <xsl:for-each select="MEMBERS/MEMBER">
                <xsl:if test="@name = 'Identifier'">
                    <xsl:value-of select="VALUE" />
                </xsl:if>
            </xsl:for-each>
        </xsl:if>
    </xsl:for-each>
    <xsl:text>" & vbCr &</xsl:text>
    <xsl:text>" -------------------------------------------------------- " & vbCr &</xsl:text>
    <!-- Data -->
    <xsl:for-each select="DEFINITION/MEMBERS/MEMBER">
        <xsl:if test="@type = 'OBJECT'">
            <xsl:for-each select="VALUE/DEFINITION">
                <xsl:if test="not(contains(@class, 'Device'))">
                    <xsl:for-each select="MEMBERS/MEMBER">
                        <xsl:if test="@type != 'TIME' and string-length(VALUE) < 30">
                            <xsl:text>"</xsl:text>
                            <xsl:value-of select="parent::node( )/parent::node( )/@class" />
                            <xsl:text>-</xsl:text>
                            <xsl:value-of select="@name" />
                            <xsl:text>:</xsl:text>
                            <xsl:value-of select="translate(VALUE, ' ', '')" />
                            <xsl:text>" & vbCr &</xsl:text>
                        </xsl:if>
                    </xsl:for-each>
                </xsl:if>
            </xsl:for-each>
        </xsl:if>
```

-continued

```
      </xsl:for-each>
    </xsl:if>
  </xsl:for-each>
  <xsl:text>" ")</xsl:text>
  </xsl:template>
</xsl:stylesheet>
```

Applying this example transformation to a particular set of medical status data can result in the following VBScript file:

```
MsgBox("Data Object Received:" & vbCr & vbCr &
    "Current localtime: 20100519142454723" & vbCr &
    "Device GUID: 38E63C6BF6A34450A9F5E76C6C8F363A" &
    vbCr &
    "Patient ID: " & vbCr & "Clinician ID: " & vbCr & "-----------------
---------------------------------------" & vbCr &
    "    CNIBPDStd->Status: 1" & vbCr &
    "    CNIBPDStd->Systolic: 12072" & vbCr &
    "    CNIBPDStd->Diastolic: 8147" & vbCr &
    "    CNIBPDStd->MAP: 9455" & vbCr &
    "    CNIBPDStd->HR: 80" & vbCr &
    "    CNIBPDStd->ExtStatus: 0" & vbCr &
    "    CNIBPDStd->Source: 12" & vbCr &
    "    CNIBPDStd->Mode: 10" & vbCr &
    "    CNIBPDStd->Method: 10" & vbCr &
    "    CTempDStd->Status: 0" & vbCr &
    "    CTempDStd->ExtStatus: 0" & vbCr &
    "    CTempDStd->Source: 0" & vbCr &
    "    CTempDStd->Mode: 1" & vbCr &
    "    CTempDStd->Method: 1" & vbCr &
    "    CTempDStd->Temperature: +0.000000000E+000" & vbCr
        &
    "    CSpO2DStd->Status: 0" & vbCr &
    "    CSpO2DStd->Sat: 0" & vbCr &
    "    CSpO2DStd->HR: 0" & vbCr &
    "    CSpO2DStd->ExtStatus: 0" & vbCr &
    "    CSpO2DStd->Source: 13" & vbCr &
    "    CSpO2DStd->Mode: 0" & vbCr &
    "    CSpO2DStd->Method: 3" & vbCr &
    "    CWeightDStd->Status: 0" & vbCr &
    "    CWeightDStd->Weight: 0" & vbCr &
    "    CWeightDStd->Stabilization: 0" & vbCr &
    "    CWeightDStd->ExtStatus: 0" & vbCr &
    "    CWeightDStd->Mode: 0" & vbCr &
    "    CWeightDStd->Method: 0" & vbCr &
    "    CWeightDStd->Source: 0" & vbCr &
    "    CHeightDStd->Status: 0" & vbCr &
    "    CHeightDStd->Height: 0" & vbCr &
    "    CHeightDStd->ExtStatus: 0" & vbCr &
    "    CHeightDStd->Mode: 0" & vbCr &
    "    CHeightDStd->Method: 0" & vbCr &
    "    CHeightDStd->Source: 0" & vbCr &
    "    CBMIDStd->Status: 0" & vbCr &
    "    CBMIDStd->Weight: 0" & vbCr &
    "    CBMIDStd->Height: 0" & vbCr &
    "    CBMIDStd->BodyMassIndex: 0" & vbCr &
    "    CBMIDStd->ExtStatus: 0" & vbCr &
    "    CBMIDStd->Source: 0" & vbCr &
    "    CBMIDStd->Mode: 0" & vbCr &
    "    CBMIDStd->Method: 0" & vbCr &
    "    CRespDStd->Status: 0" & vbCr &
    "    CRespDStd->ExtStatus: 0" & vbCr &
    "    CRespDStd->Source: 0" & vbCr &
    "    CRespDStd->Mode: 0" & vbCr &
    "    CRespDStd->Method: 0" & vbCr &
    "    CRespDStd->Respiration: 0" & vbCr &
    "    CPainDStd->Status: 0" & vbCr &
    "    CPainDStd->ExtStatus: 0" & vbCr &
    "    CPainDStd->Source: 0" & vbCr &
    "    CPainDStd->Mode: 0" & vbCr &
    "    CPainDStd->Method: 0" & vbCr &
    "    CPainDStd->PainIndex: 0" & vbCr &
    "    CClinicianDStd->Status: 0" & vbCr &
    "    CClinicianDStd->ExtStatus: 0" & vbCr &
    "    CClinicianDStd->Source: 0" & vbCr &
    "    CClinicianDStd->Mode: 0" & vbCr &
```

-continued

```
    "    CClinicianDStd->Method: 0" & vbCr &
    "    CClinicianDStd->Identifier: " & vbCr &
    "    CPatientDStd->Status: 0" & vbCr &
    "    CPatientDStd->ExtStatus: 0" & vbCr &
    "    CPatientDStd->Source: 0" & vbCr &
    "    CPatientDStd->Mode: 0" & vbCr &
    "    CPatientDStd->Method: 0" & vbCr &
    "    CPatientDStd->Identifier: " & vbCr & " ")
```

In various embodiments, the script files 212 can contain various types of scripts. For example, one or more of the script files 212 can include a VBScript script, as shown in the example above. In another example, one or more of the script files 212 can include a JavaScript script. In yet another example, one or more of the script files 212 can be a batch file. A batch file is a text file containing a sequence of operating system commands, possibly including parameters and operators supported by a batch command language. The operating system commands in the batch files generated by the transformer system 104 can cause the transformer system 104 to run one or more other programs. A program is a sequence of instructions that can be executed by a computer.

After the transformer system 104 generates the script files 212, the transformer system 104 can cause the computing device 200 to perform various actions with regard to the script files 212. For example, the transformer system 104 can cause the computing device 200 to store the script files 212. Furthermore, after the transformer system 104 generates the script files 212, the transformer system 104 can cause the computing device 200 to execute the script files 212. In some embodiments, the transformer system 104 causes the computing device 200 to execute one or more of the script files 212 without requiring a user to provide any input to the computing device 200 after the computing device 200 receives the medical status data 108. In other words, the transformer system 104 can automatically cause the computing device 200 to run one or more of the script files 212. Furthermore, in some embodiments, the computing device 200 is able to run one or more of the script files 212 in response to input from a user. In such embodiments, the transformer system 104 may or may not automatically cause the computing device 200 to run the script files 212.

When the computing device 200 runs a given one of the script files 212, the given script file can cause the computing device 200 to perform various actions. For example, the given script file can cause the computing device 200 to generate the result data 116 and use the video adapter 208 to display the result data 116 in a window in a graphical user interface presented by the transformer system 104. The video adapter 208 is an electronics component that generates video signals sent to a video display. For instance, in this example, the medical status data 108 can represent an ECG of the patient 110. Furthermore, in this example, the given script file can cause the computing device 200 to use the ECG of the patient 110 to determine whether the patient 110 is suffering from a heart arrhythmia based on the medical status data 108. In this example, the given script file can cause the computing device 200 to use the video adapter 208 to display result data that indicates whether the patient 110 is suffering from a heart arrhythmia.

In another example, the given script file can cause the computing device 200 to generate result data 116 that is compatible with one or more of the receiver systems 106. For instance, in this example, the medical status data 108 can represent a blood oxygen saturation level of the patient 110 and one of the receiver systems 106 accepts measurements of blood oxygen saturation levels in a given format. Furthermore, in this example, the given script file can cause the computing device 200 to generate result data 116 that represents the blood oxygen saturation level of the patient 110 in the given format. The given script file can then cause the computing device 200 to use the communication interface 206 to provide the result data 116 to the receiver system.

In yet another example, the given script file can cause the computing device 200 to dynamically generate one or more programs. In this example, the given script file can, in some embodiments, automatically cause the computing device 200 to execute the one or more dynamically-generated programs. In other embodiments, the computing device 200 can execute the dynamically-generated programs in response to input from a user or in response to another event.

Furthermore, when the computing device 200 runs the given script file, the given script file can cause the computing device 200 to run one or more additional programs. To run the additional programs, the processing system 204 executes computer-readable instructions in the additional programs. The additional programs can be implemented in various ways. For example, one or more of the additional programs can be implemented in various scripting languages, such as JavaScript, ECMAScript, VBScript, Rexx, Perl, Python, or another scripting language. In another example, one or more of the additional programs can be compiled versions of programs written in high-level programming languages, such as C, C++, C#, Java, Visual Basic, or another high-level programming language. In yet another example, one or more of the additional programs can be batch files.

The additional programs can have various origins. For example, one or more of the additional programs can be included in an operating system of the transformer system 104. In another example, one or more of the additional programs can be programs that execute on the transformer system 104, but are not part of the operating system of the transformer system 104. In this example, one or more of the additional programs can be developed by an entity that manufactures and/or administrates the monitoring device 102, an entity that manufactures and/or administrates the transformer system 104, an entity that manufactures and/or administrates the receiver systems 106, or another entity.

In addition to the programs stored in the data storage system 202 of the transformer system 104, execution of one or more of the script files 212 can cause the transformer system 104 to invoke programs that run on other computing devices. For example, another computing device (not shown) hosts a database access program. In this example, the database access program returns data in response to queries issued by the transformer system 104 when the transformer system 104 runs the script files 212. In another example, another computing device hosts a program that converts temperature measurements in Fahrenheit into temperature measurements in Celsius. In this example, when the computing device 200 executes one of the script files 212, the transformer system 104 sends a temperature measurement in Fahrenheit to the other computing device and receives a corresponding temperature measurement in Celsius.

In some embodiments, the transformer system 104 maintains a list of the receiver systems 106. In such embodiments, the transformer system 104 applies the transformations specified by the XSLT documents 210 to the medical status data 108 for each receiver system in the list of receiver systems. Furthermore, in such embodiments, some of the receiver systems 106 may not need to receive transformed data whenever the transformer system 104 receives patient monitoring data. For instance, some of the receiver systems 106 may not need to receive any data when the medical status data 108 does not indicate that the patient 110 has an abnormal condition. In such embodiments, the transformations specified by the XSLT documents 210 can provide that no transformed data is generated when a particular receiver system or type of receiver system does not need to receive transformed data based on the medical status data 108. The XSLT documents 210 can use globally unique identifiers, serial numbers, product numbers, or other information individually or categorically identifying the receiver systems 106 to specify how to transform the medical status data 108.

Figure 3:
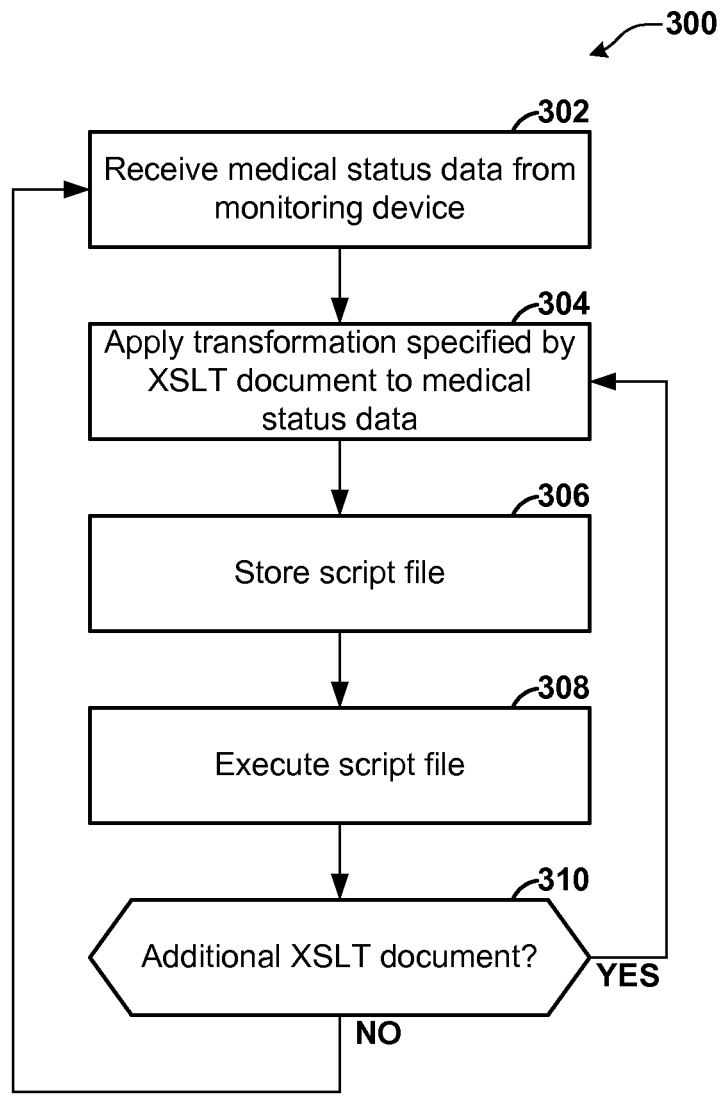
FIG. 3 is a flowchart illustrating an example operation of the transformer system to handle incoming medical status data.

FIG. 3 is a flowchart illustrating an example operation 300 of the transformer system 104 to handle incoming medical status data. As illustrated in the example of FIG. 3, the operation 300 begins when the transformer system 104 receives the medical status data 108 from the monitoring device 102 (302). After the transformer system 104 receives the medical status data 108 from the monitoring device 102, the transformer system 104 generates a given one of the script files 212 by applying a transformation specified by one of the XSLT documents 210 to the medical status data 108 (304). Next, the transformer system 104 stores the given script file as a local file at the transformer system 104 (306).

After the transformer system 104 generates the given script file, the transformer system 104 executes the given script file (308). The transformed data 112 results from executing the given script file. As discussed elsewhere in this specification, execution of the given script file can cause the transformer system 104 perform various actions, such as displaying information to a user of the computing device 200, providing the result data to one or more of the receiver systems 106, and storing result data in one or more local files at the computing device 200.

After the transformer system 104 generates the script file 212, the transformer system 104 determines whether there is an additional XSLT document (310). The additional XSLT document is an XSLT document that specifies a transformation that the transformer system 104 has not yet applied to the medical status data 108. If there is no additional XSLT document ("NO" of 310), the transformer system 104 waits to receive additional medical status data from the monitoring device 102 or another monitoring device (302). When the transformer system 104 receives such additional medical status data, the operation 300 recurs with regard to the additional medical status data. Otherwise, if there is an additional XSLT document ("YES" of 310), the transformer system 104 repeats the steps 304, 306, 308, and 310 with regard to the additional XSLT document.

Figure 4:
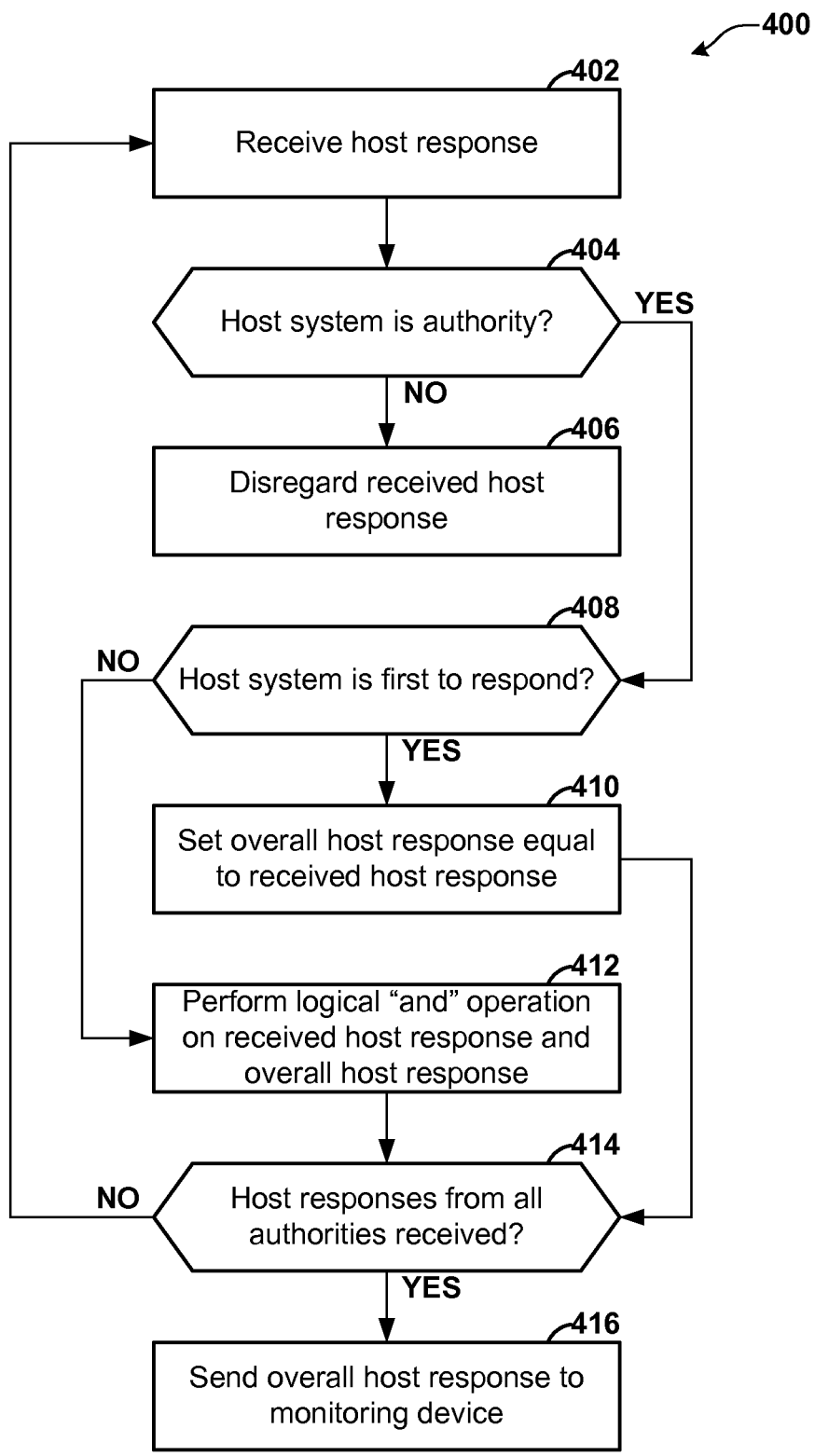
FIG. 4 is a flowchart illustrating an example operation of the transformer system to handle host responses.

FIG. 4 is a flowchart illustrating an example operation 400 of the transformer system 104 to handle host responses. As discussed elsewhere in this specification, the transformer system 104 can provide the data to multiple receiver systems 106. For example, transformed versions of the medical status data 108 can be provided by the transformer system 104 to the receiver systems 106. In another example, result data that results from executing script files can be provided by the transformer system 104 to the receiver system 106. When the receiver systems 106 receive the data, the receiver systems 106 generate host responses that indicate whether the data was successfully received.

As illustrated in the example of FIG. 4, the operation 400 begins when the transformer system 104 receives a host response from a given receiver system (402). The given receiver system is one of the receiver systems 106 to which the transformer system 104 sent data. The host response can indicate that the given receiver system acknowledges successfully receiving the data or can indicate that the given receiver system did not successfully receive the data.

Upon receiving the host response from the given receiver system, the transformer system 104 determines whether the receiver system is an authority (404). A receiver system is an authority when the operation of the monitoring device 102 is effected by whether or not the receiver system successfully received the data. If a receiver system is not an authority, the operation of the monitoring device 102 is not effected by whether or not the receiver system successfully received the data. In some embodiments, the transformer system 104 maintains a set of authority attributes for each of the receiver systems 106. The authority attributes for the receiver systems 106 indicate whether corresponding ones of the receiver systems 106 are authorities. In some embodiments, an administrator of the transformer system 104 or another person can configure which of the receiver systems 106 are authorities.

In some embodiments, it is possible that none of the receiver systems 106 is an authority. If none of the receiver systems 106 is an authority, the transformer system 104 sends a host response to the monitoring device 102 as soon as the monitoring device 102 sends the data to the receiver systems 106. This host response can indicate that the receiver systems 106 successfully received the data. The transformer system 104 can send such a host response before receiving any host responses from the receiver systems 106 because the operation of the monitoring device 102 is not going to be effected by the actual host responses of any of the receiver systems 106.

If the given receiver system is not an authority ("NO" of 404), the transformer system 104 can disregard the host response (406). In other words, the transformer system 104 does not need to forward the received host response to the monitoring device 102. The transformer system 104 can disregard the host response when the given receiver system is not an authority because the operation of the monitoring device 102 is not effected one way or the other if the given receiver system successfully received the data.

On the other hand, if the given receiver system is an authority ("YES" of 404), the transformer system 104 determines whether the given receiver system is the first one of the receiver systems 106 to send a host response in response to the data (408). If the given receiver system is the first one of the receiver systems 106 to send a host response in response to the data ("YES" of 408), the transformer system 104 sets an overall host response equal to the received host response (410). For example, if the received host response indicates successful reception of the data, the transformer system 104 sets the overall host response to indicate successful reception of the data. Likewise, if the received host response indicates unsuccessful reception of the data, the transformer system 104 sets the overall host response to indicate unsuccessful reception of the data.

On the other hand, if the receiver system 408 is not the first one of the receiver systems 106 to send a host response in response to the data ("NO" of 408), the transformer system 104 sets the overall host response to a result of performing a logical "and" operation on the received host response and the overall host response (412). For example, if the overall host response indicates successful reception of the data and the received host response indicates successful reception of the data, the transformer system 104 sets the overall host response to indicate successful reception of the data. If the overall host response indicates successful reception of the data and the received host response indicates unsuccessful reception of the data, the transformer system 104 sets the overall host response to indicate unsuccessful reception of the data. If the overall host response indicates unsuccessful reception of the data and the received host response indicates successful reception of the data, the transformer system 104 sets the overall host response to indicate unsuccessful reception of the data. If the overall host response indicates unsuccessful reception of the data and the received host response indicates unsuccessful reception of the data, the transformer system 104 sets the overall host response to indicate unsuccessful reception of the data.

After either setting the overall host response equal to the received host response in step 410 or setting the overall host response equal to the result of performing a logical "and" operation on the overall host response and the received host response in step 412, the transformer system 104 determines whether the transformer system 104 has received host responses from each of the receiver systems 106 that are authorities (414). If the transformer system 104 has received host responses from each of the receiver systems 106 that are authorities ("YES" of 414), the transformer system 104 sends the overall host response to the monitoring device 102 (416). Otherwise, if the transformer system 104 has not received host responses from each of the receiver systems 106 that are authorities ("NO" of 414), the transformer system 104 waits to receive another host response (402). When the transformer system 104 receives another host response, the operation 400 recurs with regard to the other host response.

Figure 5:
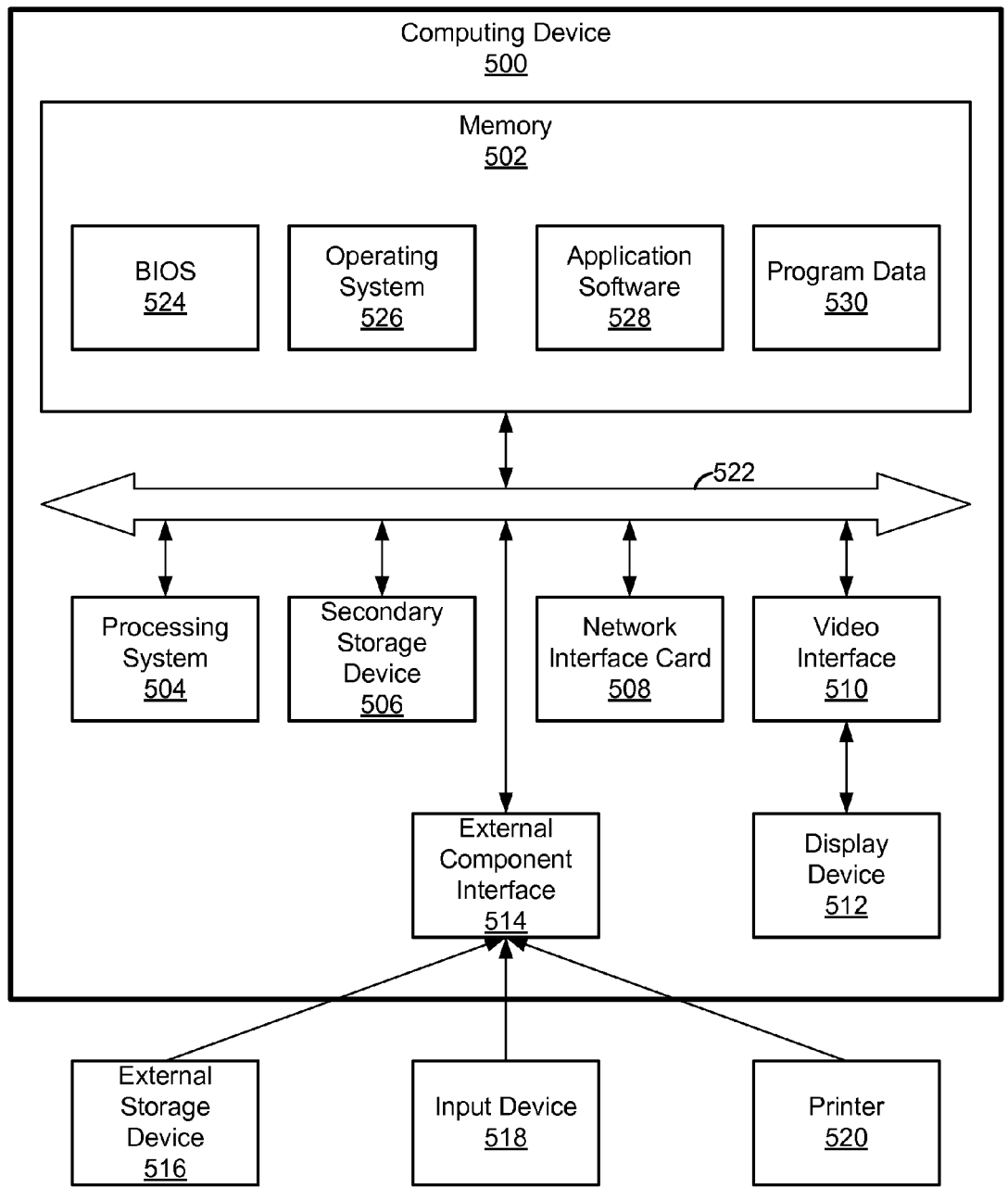
FIG. 5 is a block diagram illustrating an example computing system.

FIG. 5 is a block diagram illustrating an example computing device 500. In some embodiments, the transformer system 104 and/or the receiver systems 106 provided by computing devices that are implemented like the computing device 500. It should be appreciated that in other embodiments, the transformer system 104 and/or the receiver systems 106 are provided by computing devices having hardware components other than those illustrated in the example of FIG. 5.

In different embodiments, computing devices are implemented in different ways. For instance, in the example of FIG. 5, the computing device 500 comprises a memory 502, a processing system 504, a secondary storage device 506, a network interface card 508, a video interface 510, a display device 512, an external component interface 514, an external storage device 516, an input device 518, a printer 520, and a communication medium 522. In other embodiments, computing devices are implemented using more or fewer hardware components. For instance, in another example embodiment, a computing device does not include a video interface, a display device, an external storage device, or an input device.

The memory 502 includes one or more computer-readable data storage media capable of storing data and/or instructions. As used in this document, a computer-readable data storage medium is a device or article of manufacture that stores data and/or software instructions readable by a computing device. In different embodiments, the memory 502 is implemented in different ways. For instance, in various embodiments, the memory 502 is implemented using various types of computer-readable data storage media. Example types of computer-readable data storage media include, but are not limited to, dynamic random access memory (DRAM), double data rate synchronous dynamic random access memory (DDR SDRAM), reduced latency DRAM, DDR2 SDRAM, DDR3 SDRAM, Rambus RAM, solid state memory, flash memory, read-only memory (ROM), electrically-erasable programmable ROM, and other types of devices and/or articles of manufacture that store data.

The processing system 504 includes one or more physical integrated circuits that selectively execute software instructions. In various embodiments, the processing system 504 is implemented in various ways. For instance, in one example embodiment, the processing system 504 is implemented as one or more processing cores. For instance, in this example embodiment, the processing system 504 may be implemented as one or more Intel Core 2 microprocessors. In another example embodiment, the processing system 504 is implemented as one or more separate microprocessors. In yet another example embodiment, the processing system 504 is implemented as an ASIC that provides specific functionality. In yet another example embodiment, the processing system 504 provides specific functionality by using an ASIC and by executing software instructions.

In different embodiments, the processing system 504 executes software instructions in different instruction sets. For instance, in various embodiments, the processing system 504 executes software instructions in instruction sets such as the x86 instruction set, the POWER instruction set, a RISC instruction set, the SPARC instruction set, the IA-64 instruction set, the MIPS instruction set, and/or other instruction sets.

The secondary storage device 506 includes one or more computer-readable data storage media. The secondary storage device 506 stores data and software instructions not directly accessible by the processing system 504. In other words, the processing system 504 performs an I/O operation to retrieve data and/or software instructions from the secondary storage device 506. In various embodiments, the secondary storage device 506 is implemented by various types of computer-readable data storage media. For instance, the secondary storage device 506 may be implemented by one or more magnetic disks, magnetic tape drives, CD-ROM discs, DVD-ROM discs, Blu-Ray discs, solid state memory devices, Bernoulli cartridges, and/or other types of computer-readable data storage media.

The network interface card 508 enables the computing device 500 to send data to and receive data from a computer communication network. In different embodiments, the network interface card 508 is implemented in different ways. For example, in various embodiments, the network interface card 508 is implemented as an Ethernet interface, a token-ring network interface, a fiber optic network interface, a wireless network interface (e.g., WiFi, WiMax, etc.), or another type of network interface.

The video interface 510 enables the computing device 500 to output video information to the display device 512. In different embodiments, the video interface 510 is implemented in different ways. For instance, in one example embodiment, the video interface 510 is integrated into a motherboard of the computing device 500. In another example embodiment, the video interface 510 is a video expansion card. Example types of video expansion cards include Radeon graphics cards manufactured by Advanced Micro Devices, Inc. of Sunnyvale, Calif., Geforce graphics cards manufactured by Nvidia Corporation of Santa Clara, Calif., and other types of graphics cards.

In various embodiments, the display device 512 is implemented as various types of display devices. Example types of display devices include, but are not limited to, cathode-ray tube displays, LCD display panels, plasma screen display panels, touch-sensitive display panels, LED screens, projectors, and other types of display devices. In various embodiments, the video interface 510 communicates with the display device 512 in various ways. For instance, in various embodiments, the video interface 510 communicates with the display device 512 via a Universal Serial Bus (USB) connector, a VGA connector, a digital visual interface (DVI) connector, an S-Video connector, a High-Definition Multimedia Interface (HDMI) interface, a DisplayPort connector, or other types of connectors.

The external component interface 514 enables the computing device 500 to communicate with external devices. In various embodiments, the external component interface 514 is implemented in different ways. For instance, in one example embodiment, the external component interface 514 is a USB interface. In other example embodiments, the computing device 500 is a FireWire interface, a serial port interface, a parallel port interface, a PS/2 interface, and/or another type of interface that enables the computing device 500 to communicate with external components.

In different embodiments, the external component interface 514 enables the computing device 500 to communicate with different external components. For instance, in the example of FIG. 5, the external component interface 514 enables the computing device 500 to communicate with the external storage device 516, the input device 518, and the printer 520. In other embodiments, the external component interface 514 enables the computing device 500 to communicate with more or fewer external components. Other example types of external components include, but are not limited to, speakers, phone charging jacks, modems, media player docks, other computing devices, scanners, digital cameras, a fingerprint reader, and other devices that can be connected to the computing device 500.

The external storage device 516 is an external component comprising one or more computer readable data storage media. Different implementations of the computing device 500 interface with different types of external storage devices. Example types of external storage devices include, but are not limited to, magnetic tape drives, flash memory modules, magnetic disk drives, optical disc drives, flash memory units, zip disk drives, optical jukeboxes, and other types of devices comprising one or more computer-readable data storage media. The input device 518 is an external component that provides user input to the computing device 500. Different implementations of the computing device 500 interface with different types of input devices. Example types of input devices include, but are not limited to, keyboards, mice, trackballs, stylus input devices, key pads, microphones, joysticks, touch-sensitive display screens, and other types of devices that provide user input to the computing device 500. The printer 520 is an external device that prints data to paper. Different implementations of the computing device 500 interface with different types of printers. Example types of printers include, but are not limited to laser printers, ink jet printers, photo printers, copy machines, fax machines, receipt printers, dot matrix printers, or other types of devices that print data to paper.

The communications medium 522 facilitates communication among the hardware components of the computing device 500. In different embodiments, the communications medium 522 facilitates communication among different components of the computing device 500. For instance, in the example of FIG. 5, the communications medium 522 facilitates communication among the memory 502, the processing system 504, the secondary storage device 506, the network interface card 508, the video interface 510, and the external component interface 514. In different implementations of the computing device 500, the communications medium 522 is implemented in different ways. For instance, in different implementations of the computing device 500, the communications medium 522 may be implemented as a PCI bus, a PCI Express bus, an accelerated graphics port (AGP) bus, an Infiniband interconnect, a serial Advanced Technology Attachment (ATA) interconnect, a parallel ATA interconnect, a Fiber Channel interconnect, a USB bus, a Small Computing system Interface (SCSI) interface, or another type of communications medium.

The memory 502 stores various types of data and/or software instructions. For instance, in the example of FIG. 5, the memory 502 stores a Basic Input/Output System (BIOS) 524, an operating system 526, application software 528, and program data 530. The BIOS 524 includes a set of software instructions that, when executed by the processing system 504, cause the computing device 500 to boot up. The operating system 526 includes a set of software instructions that, when executed by the processing system 504, cause the computing device 500 to provide an operating system that coordinates the activities and sharing of resources of the computing device 500. Example types of operating systems include, but are not limited to, Microsoft Windows®, Linux, Unix, Apple OS X, Apple OS X iPhone, Palm webOS, Palm OS, Google Chrome OS, Google Android OS, and so on. The application software 528 includes a set of software instructions that, when executed by the processing system 504, cause the computing device 500 to provide applications to a user of the computing device 500. The program data 530 is data generated and/or used by the application software 528.

The various embodiments described above are provided by way of illustration only and should not be construed as limiting. Those skilled in the art will readily recognize various modifications and changes that may be made without following the example embodiments and applications illustrated and described herein. For example, the operations shown in the figures are merely examples. In various embodiments, similar operations can include more or fewer steps than those shown in the figures. Furthermore, in other embodiments, similar operations can include the steps of the operations shown in the figures in different orders.

The invention claimed is:

1. A method comprising:
   providing a computing device;
   receiving, by the computing device, medical status data generated by a monitoring device, the medical status data representing a physiological characteristic of a patient;
   generating, by the computing device, a script file by applying a transformation to the medical status data, the transformation specified by an Extensible Stylesheet Language Transformation (XSLT) document;
   executing, by the computing device, the script file;
   receiving responses from a plurality of receiver systems, each of the responses indicating whether each of the receiver systems successfully received data sent by the computing device;
   determining whether one or more of the receiver systems is an authority, wherein one receiver system is an authority when operation of the monitoring device is effected by whether the one receiver system successfully received the data;
   disregarding one or more of the responses when one or more of the receiver systems is not an authority;
   setting, when one response is a first response received from receiver systems to which the computing device has sent data and the one receiver system is an authority, an overall response to the response;
   setting, when the one response is not the first response received from the receiver systems to which the computing device sent data and the one receiver system is an authority, the overall response to a result of performing a logical "and" operation on the response and the overall response; and
   sending the overall response to the monitoring device when the computing device has received responses from each of the receiver systems to which the computing device sent data.

2. The method of claim 1, wherein the physiological characteristic is one of: a blood pressure of the patient, a blood oxygen saturation level of the patient, a pulse rate of the patient, a body temperature of the patient, and an electrocardiogram (ECG) of the patient.

3. The method of claim 1,
   wherein the physiological characteristic is an ECG of the patient; and
   wherein executing the script file causes the computing device to determine, based on the medical status data, whether the patient is suffering a heart arrhythmia.

4. The method of claim 1, wherein the script file is a batch file.

5. The method of claim 1, wherein executing the script file comprises:
   generating result data; and
   storing, by the computing device, the result data in a file.

6. The method of claim 1, wherein executing the script file comprises:
   generating result data; and
   providing the result data to one of the receiver systems.

7. The method of claim 6, further comprising:
   generating, by the computing device, another script file by applying a different transformation to the medical status data, the different transformation specified by another XSLT document; and
   executing, by the computing device, the other script file.

8. The method of claim 7, wherein executing the other script file comprises:
   generating different data; and
   providing the different data to another of the receiver systems.

9. The method of claim 1, further comprising:
   generating a transformed version of the medical status data by applying another transformation to the medical status data; and
   providing the transformed version of the medical status data to one of the receiver systems.

10. The method of claim 1, wherein the computing device executes the script file without requiring a user to provide any input to the computing device after the computing device receives the medical status data.

11. A computing device comprising:
   a processing system;
   a communication interface that receives medical status data from a monitoring device, the medical status data representing a physiological characteristic of a patient; and
   a data storage system that stores:
      an Extensible Stylesheet Language Transformation (XSLT) document;

and
computer-readable instructions that, when executed by the processing system, cause the computing device to:
generate a script file by applying a transformation to the medical status data, the transformation specified by the XSLT document;
execute the script file, wherein executing the script file causes the computing device to generate transformed data by applying a different transformation to the medical status data and send transformed data to a plurality of receiver systems;
determine whether a given one of the receiver systems is an authority, wherein the given receiver system is an authority when operation of the monitoring device is effected by whether the given receiver system successfully received the transformed data;
disregard a response received from the given receiver system when the given receiver system is not an authority, the received response indicating whether the given receiver system successfully received the transformed data;
set an overall response to the received response when the received response is a first response received from the receiver systems and the given receiver system is an authority;
set the overall response to a result of performing a logical "and" operation on the received response and the overall response when the received response is not the first response received from the receiver systems and the given receiver system is an authority; and
send the overall response to the monitoring device when the computing device has received responses from each of the receiver systems.

12. The computing device of claim 11, wherein execution of the script file causes execution of one or more programs.

13. The computing device of claim 12, wherein the one or more programs are executed by the computing device.

14. The computing device of claim 12, wherein at least one of the one or more programs is part of an operating system of the computing device.

15. The computing device of claim 12, wherein execution of the script file causes the communication interface to provide result data to the given receiver system, the result data generated by the one or more programs based on the medical status data.

16. The computing device of claim 15, wherein the computer-readable instructions, when executed by the processing system, further cause the computing device to:
generate another script file by applying a different transformation to the medical status data, the different transformation specified by another XSLT document; and
execute the other script file,
wherein execution of the other script file causes the communication interface to provide different result data to another of the receiver systems, the different result data being generated by the one or more programs based on the medical status data.

17. The computing device of claim 11, wherein the computer-readable instructions, when executed by the processing system, cause the computing device to execute the script file in response to receiving input from a user to execute the script file.

* * * * *